(12) United States Patent
Clemens et al.

(10) Patent No.: US 11,020,587 B2
(45) Date of Patent: Jun. 1, 2021

(54) IMPLANTABLE MEDICAL ELECTRODE ASSEMBLIES AND ASSOCIATED DEVICES AND METHODS

(71) Applicant: MEDTRONIC, INC., Minneapolis, MN (US)

(72) Inventors: William J. Clemens, Fridley, MN (US); Linda L. Franke, Blaine, MN (US); Mark T. Marshall, Forest Lake, MN (US); Timothy M. Ramos, Blaine, MN (US); Vania Lee, Circle Pines, MN (US)

(73) Assignee: Medtronic, Inc., Minneapolis, MN (US)

( * ) Notice: Subject to any disclaimer, the term of this patent is extended or adjusted under 35 U.S.C. 154(b) by 98 days.

(21) Appl. No.: 16/357,813

(22) Filed: Mar. 19, 2019

(65) Prior Publication Data

US 2019/0290899 A1    Sep. 26, 2019

Related U.S. Application Data

(60) Provisional application No. 62/646,142, filed on Mar. 21, 2018.

(51) Int. Cl.
*A61N 1/00* (2006.01)
*A61N 1/05* (2006.01)
(Continued)

(52) U.S. Cl.
CPC ............ *A61N 1/056* (2013.01); *A61N 1/0568* (2013.01); *A61N 1/0575* (2013.01); *A61N 1/306* (2013.01);
(Continued)

(58) Field of Classification Search
CPC .... A61N 1/056; A61N 1/0568; A61N 1/0575; A61N 1/306; A61N 1/37; A61N 1/3962; A61N 2001/058
See application file for complete search history.

(56) References Cited

U.S. PATENT DOCUMENTS

| | | |
|---|---|---|
| 5,002,067 A | 3/1991 | Berthelsen et al. |
| 5,522,874 A | 6/1996 | Gates |

(Continued)

OTHER PUBLICATIONS

(PCT/US2019/023177) PCT Notification of Transmittal of the International Search Report and the Written Opinion of the International Searching Authority, dated May 31, 2019, 13 pages.

*Primary Examiner* — Scott M. Getzow (57) ABSTRACT

A distal electrode of an electrode assembly, for example, employed by an implantable medical electrical lead device, extends distally from a distal terminal end of a sleeve of the assembly; and the sleeve, which defines a longitudinal axis of the assembly, includes a plurality of channels that provide fluid communication between a steroid eluting component, which is seated in an external groove of the sleeve, and an area distal to the distal terminal end of the sleeve. Floors of some or all of the sleeve channels may angle toward the longitudinal axis of the assembly, being closer to the axis at the distal terminal end of the sleeve. The assembly may further include a proximal electrode secured to a proximal end of the sleeve, wherein the proximal electrode may be mounted around an outer surface of the sleeve or coupled to the sleeve by means of a coupling component.

29 Claims, 8 Drawing Sheets

(51) Int. Cl.
  *A61N 1/37* (2006.01)
  *A61N 1/30* (2006.01)
  *A61N 1/39* (2006.01)

(52) U.S. Cl.
  CPC .............. *A61N 1/37* (2013.01); *A61N 1/3962* (2013.01); *A61N 2001/058* (2013.01)

(56) References Cited

U.S. PATENT DOCUMENTS

| | | |
|---|---|---|
| 6,198,973 B1 | 11/2001 | Marshall et al. |
| 6,363,287 B1 | 3/2002 | Brabec et al. |
| 2001/0044646 A1 | 11/2001 | Marshall et al. |
| 2011/0160831 A1* | 6/2011 | De Kock ............. A61N 1/0568 607/120 |
| 2012/0197155 A1* | 8/2012 | Mattes ...................... G01L 9/12 600/561 |

* cited by examiner

IMPLANTABLE MEDICAL ELECTRODE ASSEMBLIES AND ASSOCIATED DEVICES AND METHODS

FIELD OF THE DISCLOSURE

The present disclosure pertains to implantable medical electrical devices suited for the delivery of cardiac therapy, and more particularly to electrode assemblies thereof.

BACKGROUND

An implantable medical electrical system of the type suited for cardiac rhythm management typically includes a pulse generator device to which at least one flexible elongate lead device is coupled to deliver stimulation therapy from the pulse generator to the heart of a patient. The pulse generator device is typically implanted in a subcutaneous pocket, remote from the heart, and the lead device extends therefrom to a cardiac implant site, either endocardial or epicardial, at which an electrode of the lead is secured in intimate engagement with myocardial tissue, according to methods known in the art. Electrodes of this type, which may pierce the myocardial tissue at the implant site, are typically included in a device electrode assembly that has means to elute a steroid for the treatment of inflammation at the site. In one such electrode assembly, for example, as described in commonly assigned U.S. Pat. No. 7,184,839, a helical screw with a piercing tip, which forms an electrode, has a coating with a microstructure, such as titanium nitride, that holds a steroid solution, such as Beclomethasone. In other types of electrode assemblies, a steroid solution is loaded into a polymer, such as silicone rubber, that is formed into a component and mounted in proximity to the electrode.

SUMMARY

Various embodiments of implantable electrode assemblies disclosed herein include a steroid eluting component and are configured to enhance the effectiveness of steroid elution from the component to the implant site.

A distal electrode of any of the assembly embodiments disclosed herein extends distally from a distal terminal end of a sleeve of the assembly, and the sleeve, which defines a longitudinal axis of the assembly, includes a plurality of channels that provide fluid communication between the steroid eluting component, which is seated in an external groove of the sleeve, and an area distal to the distal terminal end of the sleeve. According to some embodiments, floors of some or all of the plurality of sleeve channels angle toward the longitudinal axis of the assembly, being closer to the axis at the distal terminal end of the sleeve. Some assembly embodiments further include a proximal electrode secured to a proximal end of the sleeve, wherein the proximal electrode may be mounted around an outer surface of the sleeve or coupled to the sleeve by means of a coupling component.

According to some embodiments of a device, which includes any one of the electrode assembly embodiments, an elongate insulated conductor couples the distal electrode to a connector of the device by means of a conductive coupling component of the electrode assembly, which is mounted within the sleeve bore, secured to a proximal portion of the distal electrode that extends within the sleeve bore, and which engages with an inner surface of the sleeve to prevent rotation of the distal electrode relative to the sleeve.

BRIEF DESCRIPTION OF THE DRAWINGS

The following drawings are illustrative of particular embodiments of the present disclosure and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 1:
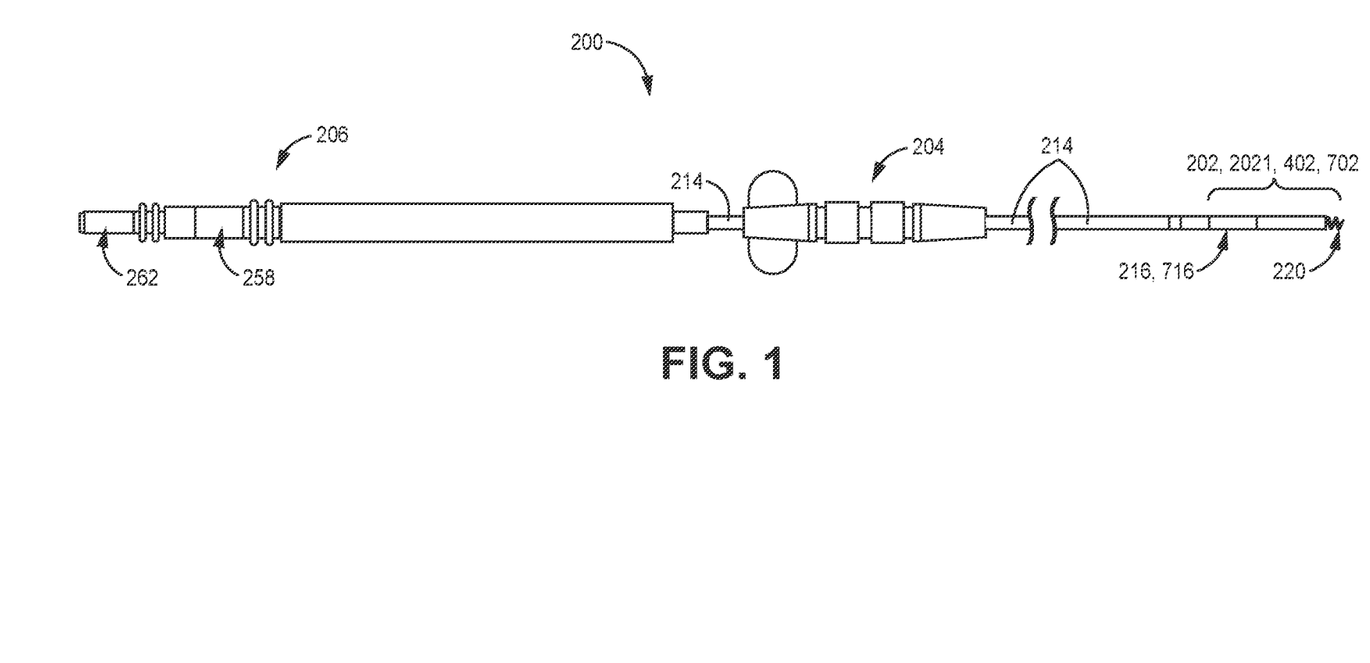
FIG. 1 is a plan view of an exemplary implantable medical electrical lead device for cardiac stimulation, which may incorporate embodiments of the present invention.

FIG. 1 is a plan view of an exemplary implantable medical electrical lead device 200 for cardiac stimulation, which may incorporate embodiments of the present invention, for example, any one of electrode assemblies 202, 2021, 402, 702, which are described in greater detail below. FIG. 1 illustrates lead device 200 including an elongate body 214 that extends proximally from electrode assembly 202, 2021, 402, 702 to a connector 206 of lead device 200. According to the illustrated embodiment, electrode assembly 202, 2021, 402, 702 includes a distal electrode 220, which is coupled to a terminal pin contact 262 of connector 206 via an elongate insulated conductor 208 (FIG. 2C), and may further include a proximal electrode 216, 716, which is coupled to a ring contact 258 of connector 206 via another elongate insulated conductor 212 (FIG. 2C). Insulated conductors 208, 212 may be assembled together in a coaxial construction of body 214, which is known to those skilled in the art. Connector 206 is also constructed according to methods known in the art and is configured for connection to the aforementioned pulse generator device. An overall length of lead device 200 may be from about 25 inches to about 40 inches, so that when the pulse generator device is implanted in a subcutaneous pocket, for example, formed in the pectoral region of a patient, lead device 200 can extend therefrom to reach a cardiac implant site at which distal electrode 220 is engaged with the myocardium. FIG. 1 further illustrates an anchoring sleeve 204 mounted around body 214 to facilitate a securement of device body 214 in proximity to the pocket according to methods known to those skilled in the art.

Figure 2A:
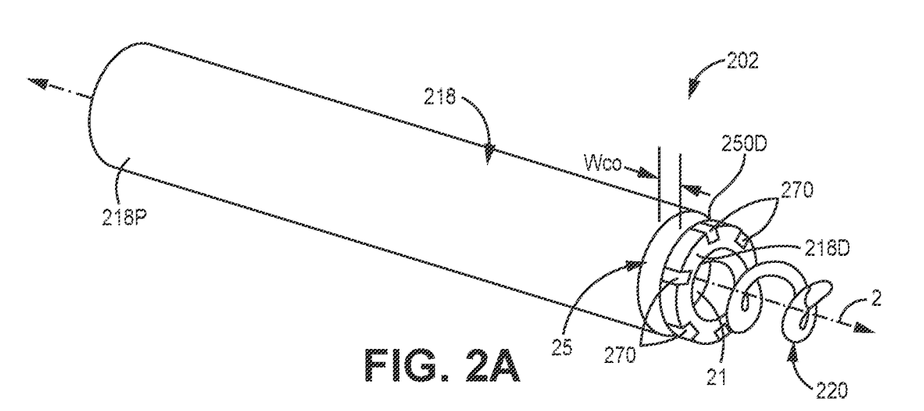
FIG. 2A is a perspective view of an electrode assembly, according to some embodiments.
Figure 2B:
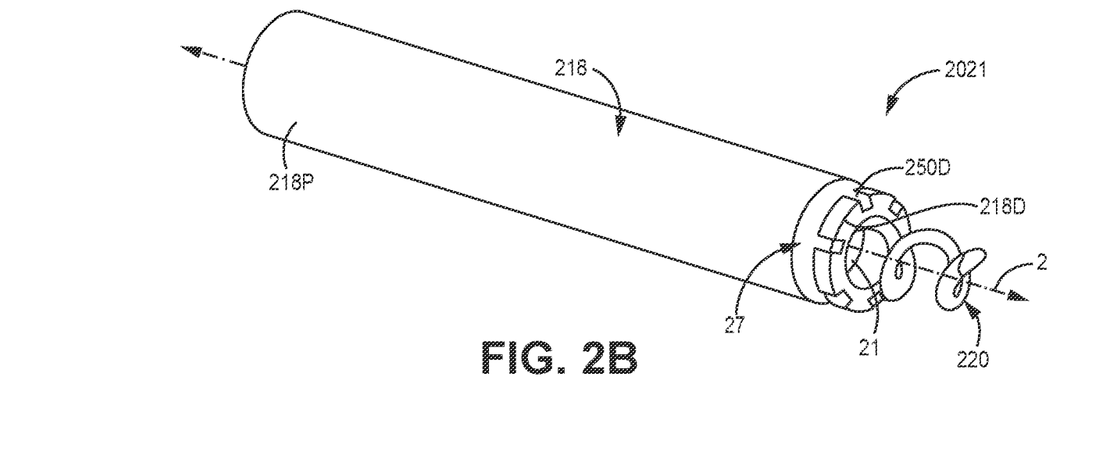
FIG. 2B is a perspective view of an electrode assembly, according to some alternate embodiments.
Figure 2C:
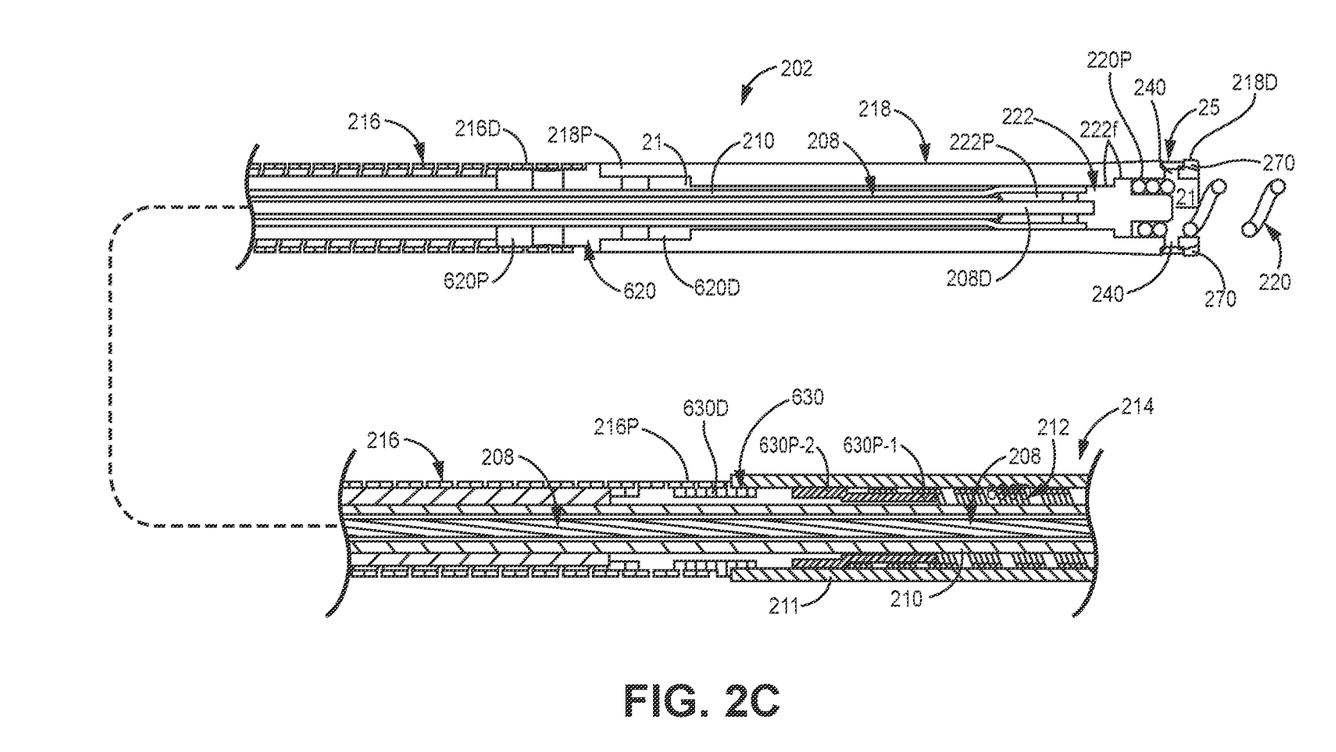
FIG. 2C is a longitudinal cross-section view of a portion of the lead device that includes the assembly of FIG. 2A, according to some embodiments.

FIG. 2A is a perspective view of electrode assembly 202, according to some embodiments; and FIG. 2B is a perspective view of electrode assembly 2021, according to some alternate embodiments. FIGS. 2A-B illustrate electrode assembly 202, 2021 including a sleeve 218, which defines a longitudinal axis 2 of assembly 202, 2021, and which has a distal terminal end 218D from which distal electrode 220 extends. According to the illustrated embodiment, distal electrode 220 is formed from a helical wire (e.g. 90/10 platinum iridum (Pt/Ir) having a diameter of about 0.010 inch) that has a piercing distal tip for engagement with the myocardium, a construction that is well known to those skilled in the art. With reference to FIG. 2C, which is a longitudinal cross-section view of a portion of lead device 200 that includes assembly 202, a proximal portion 220P of distal electrode 220 is shown being mounted within an elongate bore 21 of sleeve 218 where a conductive coupling component 222 is secured thereto, for example, via a laser weld. FIG. 2C further illustrates the aforementioned insulated conductor 208 being mechanically and electrically coupled to coupling component 222, for example, via a crimp formed between a proximal barrel 222P of component 222 and a distal end 208D of conductor 208, from which the insulation is removed. It should be understood that electrode assembly 2021 may also include the coupling between distal electrode 220 and conductor 208, via component 222, as illustrated in FIG. 2C. A similar mechanical and electrical coupling may be formed between a proximal end of conductor 208 (not shown) and the aforementioned terminal connector pin 262 of connector 206 (FIG. 1). According to an exemplary embodiment, insulated conductor 208 includes a 7×7 MP35N cable having an insulative coating of medical grade fluoropolymer, such as ethylene tetrafluoroethylene (ETFE), and may further include another layer of insulation in the form of a medical grade silicone rubber tube 210 in which the coated cable extends, a construction which is known in the art.

Figure 3A:
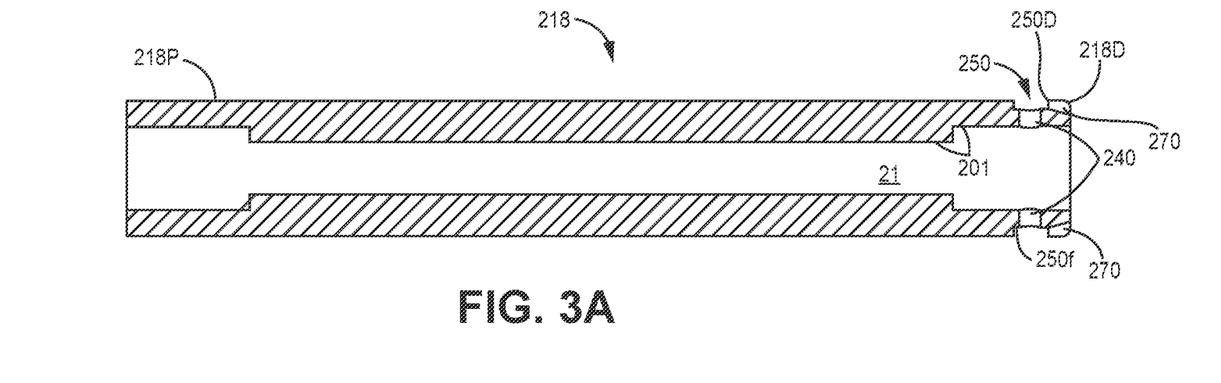
FIG. 3A is a longitudinal cross-section view through a sleeve, according to some embodiments.

With reference to a longitudinal cross-section view of sleeve 218 in FIG. 3A, sleeve 218 includes an external groove 250 that extends around bore 21; and, with further reference to FIGS. 2A-B and 3A, a plurality of channels 270 extend from a distal edge 250D of groove 250 to sleeve distal terminal end 218D, being formed in an outer surface of sleeve 218. FIG. 2A illustrates electrode assembly 202 including a steroid eluting component 25 seated within external groove 250 of sleeve 218; and FIG. 2B illustrates electrode assembly 2021 including a steroid eluting component 27, which is also seated within external groove 250 but also has a portion thereof extending within at least one of channels 270. In each of the FIGS. 2A-B embodiments, channels 270 provide fluid communication between steroid eluting component 25, 27 and an area distal to distal terminal end 218D of sleeve 218, which surrounds distal electrode 220. Thus, when electrode 220 is engaged with myocardium at the implant site, channels 270 can enhance the effectiveness of steroid elution from component 25, 27 to the implant site.

Figure 3B:
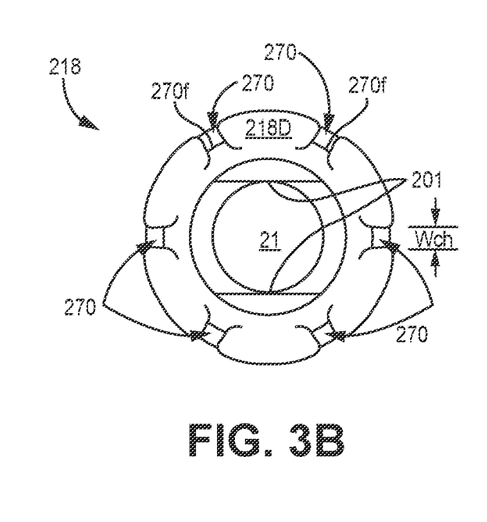
FIG. 3B is an end view of the sleeve of FIG. 3A, according to some embodiments.
Figure 3C:
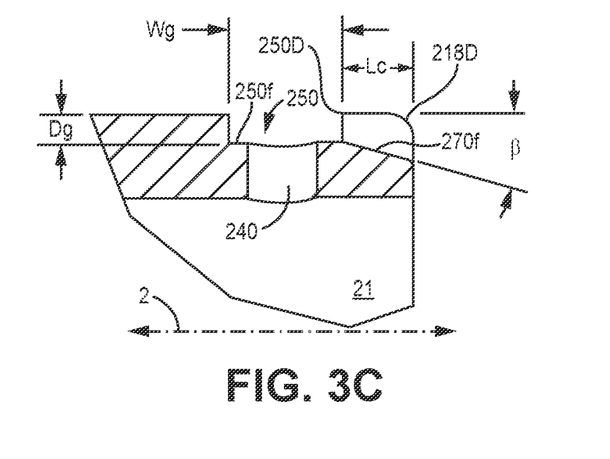
FIG. 3C is an enlarged detail view of a portion of the sleeve of FIG. 3A, in proximity to a distal terminal end thereof, according to some embodiments.

FIG. 3B is an end view of sleeve 218, according to some embodiments; and FIG. 3C is an enlarged detail view of a portion of sleeve 218 in proximity to distal terminal end 218D, according to some embodiments. FIG. 3B illustrates channels 270 uniformly spaced apart from one another around bore 21, wherein the spacing may be about sixty degrees. A width Wch of each channel 270 may be about 0.006 inch in some embodiments, and, with reference to FIG. 3C, a floor 270f of one of channels 270 is shown angling toward bore 21 of sleeve 218 (or toward longitudinal axis 2 of assembly 202 that includes sleeve 218 as shown in FIGS. 2A-B). Thus, floors 270f of some or all of channels 270 may be closer to bore 21, or axis 2, at sleeve distal terminal end 218D. The angling of channel floors 270f can facilitate the elution of steroid from component 25, 27 to a location closer to electrode 220 (FIGS. 2A-B). With further reference to FIG. 3C, according to an exemplary embodiment, an angle β that defines the angling of channel floor 270f may be about 15 degrees, a length Lc of each channel 270 may be about 0.010 inch, a depth Dg of groove 250 may be about 0.005 inch, and a width Wg of groove 250 may be about 0.016 inch.

With further reference to FIGS. 2A-B, according to some embodiments, steroid eluting component 25, 27 is formed from a medical grade silicone rubber that is loaded with a steroid, for example, a 2-part enhanced tear resistant silicone rubber (dimethyl and methyl vinyl siloxane copolymers reinforced with silica) loaded with dexamethasone acetate steroid, wherein a percentage composition by weight of the steroid may range from about 25% to about 30%. Component 25 may be molded into the form of a ring, separate from sleeve 218, and then seated within groove 250, being bonded thereto with an adhesive (e.g., a silicone medical adhesive) for securement thereto, according to some embodiments. In an exemplary embodiment, component 25 has a wall thickness of about 0.005 inch and a width Wco of about 0.014 inch to about 0.016 inch. Alternately, component 25, 27 may be insert molded into groove 250 (and channels 270 for component 27), according to methods known in the art, such that the seating and bonding of component 25, 27 is accomplished during the insert molding process. In either case, according to some preferred embodiments, an outer surface of component 25 is substantially flush with an outer surface of sleeve 218 on either side of groove 250 to maintain a substantially isodiametric profile of assembly 202, 2021. According to some embodiments in which sleeve 218 is wholly formed from a medical grade polyurethane (e.g. having a hardness of about 55 D), and in which component 25, 27 is formed from the aforementioned silicone rubber, groove 250 (and channels 270) can be plasma treated, according to methods known in the art, to enhance the surface(s) thereof for the bonding of component 25, 27 thereto. With further reference to FIG. 2C and to FIG. 3A, according to some embodiments, one or more additional channels 240 can extend through a floor 250f of groove 250, for example, to aid in the securement of component 25, 27 to sleeve 218 by allowing a flow of adhesive therethrough, or the flow of the material of component 25, 27 during molding, either of which can create a mechanical interlock between component 25, 27 and sleeve 218. In either case, one or more of channels 240 can also provide fluid communication between steroid eluting component 25, 27 and the area distal to sleeve distal terminal end 218D A diameter of each additional channel 240 may be about 0.010 inch.

With further reference to FIGS. 3A-B, according to some embodiments, an inner surface 201 of sleeve 218, which defines sleeve bore 21, is formed so that the above described conductive coupling component 222 engages therewith, for example, being formed with flat portions, as seen in FIG. 3B, to mate with flat portions 222f of coupling component 222 (FIG. 2C). The engagement between sleeve 218 and conductive coupling component 222, which may be any suitable form of mechanical interlocking in addition to, or as an alternative to that described above, functions to prevent a rotation of distal electrode 220 relative to sleeve 218, for example, when an operator engages distal electrode 220 with myocardial tissue at the implant site by rotating electrode assembly 202 around axis 2 (e.g., by means of torque transferred through device body 214 from a proximal end thereof in proximity to connector 206).

Figure 4:
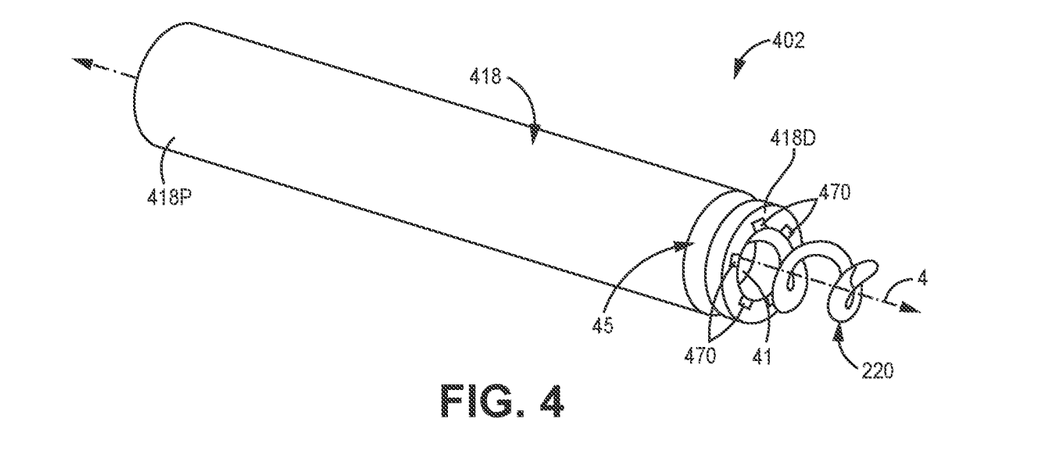
FIG. 4 is a perspective view of an electrode assembly, according to some additional embodiments.
Figure 5A:
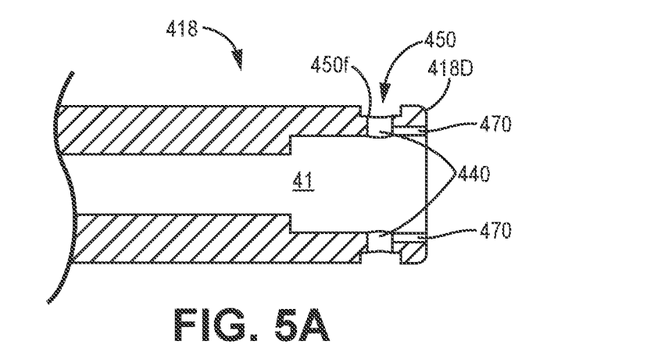
FIG. 5A is a longitudinal cross-section view through a sleeve of the FIG. 4 electrode assembly, according to some of the additional embodiments.

FIG. 4 is a perspective view of electrode assembly 402, according to some additional embodiments, which may be incorporated in lead device 200 of FIG. 1. FIG. 4 illustrates assembly 402 including a sleeve 418, which defines a longitudinal axis 4 of assembly 402, and which has a distal terminal end 418D from which distal electrode 220 extends. FIG. 4 further illustrates electrode assembly 402 including a steroid eluting component 45, which is seated in, and secured to, an external groove 450 of sleeve 418, which can be seen in a longitudinal cross-section view of sleeve 418 shown in FIG. 5A. Assembly 402 is similar in construction to that described above for assembly 202 (FIG. 2C), but an inner surface of sleeve 418, which defines an elongate bore 41 of sleeve 418, has a plurality of channels 470 formed therein (rather than in an outer surface). With further reference to FIG. 5A, additional channels 440 are shown extending through a floor 450f of groove 450 to provide fluid communication between groove 450 and channels 470, so that channels 470 essentially extend from groove 450 to sleeve distal terminal end 418D. Thus, channels 470 provide fluid communication between steroid eluting component 45 seated in groove 450 (FIG. 4) and an area distal to distal terminal end 418D of sleeve 418, which surrounds distal electrode 220. According to some embodiments and methods, component 45, for example, formed from the same materials described above for components 25, 27, is insert molded into groove 450 and channels 440, and in some cases may further extend into at least one of channels 470.

Figure 5B:
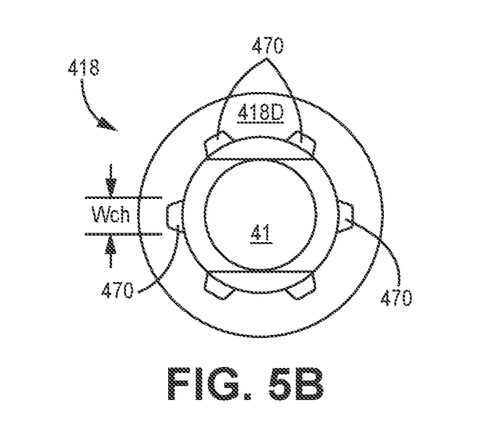
FIG. 5B is an end view of the sleeve of FIG. 5A, according to some embodiments.
Figure 5C:
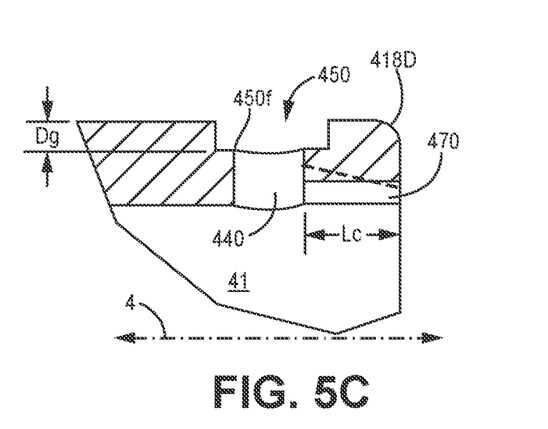
FIG. 5C is an enlarged detail view of a portion of the sleeve of FIG. 5A, in proximity to a distal terminal end thereof, according to some embodiments.

FIG. 5B is an end view of sleeve 418, according to some embodiments; and FIG. 5C is an enlarged detail view of a portion of sleeve distal terminal end 418D, according to some embodiments. FIG. 5B illustrates channels 470 uniformly spaced apart from one another around bore 41, wherein, similar to channels 270 of sleeve 218, the spacing may be about sixty degrees, and a width Wch of each channel 470 may be about 0.006 inch. According to an exemplary embodiment, as in sleeve 218, a length Lc of each channel 470 may be about 0.010 inch, a depth Dg of groove 450 may be about 0.005 inch, and a diameter of each additional channel 440 may be about 0.010 inch. With reference to FIG. 5C, a dashed line indicates an optional angling for a floor of at least one of channels 470 toward longitudinal axis 4 of assembly 402 that includes sleeve 418. Thus, floors of some or all of channels 470 can be closer to axis 4, at sleeve distal terminal end 418D, for example, to facilitate the elution of steroid from component 45 to a location closer to electrode 220.

With reference back to FIG. 1, the above described electrode assemblies 202, 2021, 402 may also include one of the aforementioned proximal electrodes 216, 716, wherein proximal electrode 216 (FIG. 2C) is configured for delivery of defibrillation therapy, and proximal electrode 716 (FIGS. 7A and 7C) is configured for delivery of pacing therapy. With reference to FIG. 2C, proximal electrode 216 is shown being secured to sleeve 218 by means of a coupling component 620 mounted within sleeve bore 21 in proximity to a proximal end 218P thereof.

Figure 6A:
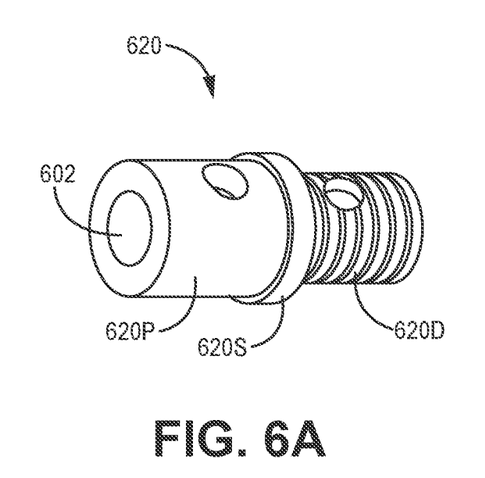
FIG. 6A is a perspective view of a coupling component, according to some embodiments.

FIG. 6A is a perspective view of coupling component 620, according to some embodiments. FIG. 6A illustrates component 620 including a proximal portion 620P, a distal portion 620D, and a shoulder 620S located therebetween. Coupling component 620 further includes an elongate bore 602, which extends along a length thereof to allow passage of insulated conductor 208 therethrough, as seen in FIG. 2C. FIG. 2C further illustrates coupling component proximal portion 620P extending proximally from sleeve proximal end 218P, and coupling component distal portion 620D being mounted within sleeve bore 21, for example, being secured to sleeve 218 by a bond that may be enhanced by threads formed along an outer surface of distal portion 620D. The bond between sleeve proximal end 218P and coupling component distal portion 620D may be formed by insert molding sleeve 218 over coupling component 620, or by using a polyurethane medical grade adhesive, wherein coupling component distal portion 620D may have a layer medical grade polyurethane formed thereover prior to forming the bond, when sleeve 218 is also formed from medical grade polyurethane. Proximal electrode 216, being suitable for the delivery of defibrillation therapy, is shown being formed by a coiled wire (e.g. 90/10 Pt/Ir or tantalum wire having a rectangular cross-section), and having a distal end 216D mounted around, and coupled to coupling component proximal portion 620P, for example, by laser welding methods known in the art. According to an exemplary embodiment, a distance between sleeve distal terminal end 218D and proximal electrode distal end 216D may be about 0.45 inch (11 mm-12 mm), and a length of proximal electrode 216 may range from about 2 inches to about 2.5 inches (51 mm-63.5 mm).

Figure 6B:
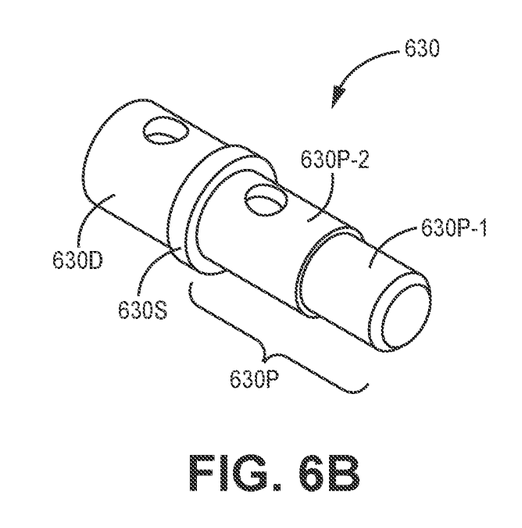
FIG. 6B is a perspective view of another coupling component, according to some embodiments.

With further reference to FIG. 2C, a proximal end 216P of proximal electrode 216 of electrode assembly 202 may be coupled to elongate insulated conductor 212 by means of another coupling component 630, a perspective view of which is shown in FIG. 6B. FIG. 6B illustrates the other coupling component 630 including a distal portion 630D, a stepped proximal portion 630P, and a shoulder 630S located therebetween. With reference to FIG. 2C, proximal electrode proximal end 216P is mounted around and coupled to distal portion 630D of the other coupling component 630, for example, by laser welding methods known in the art. With reference to FIG. 6B in conjunction with FIG. 2C, a first surface 630P-1 of the other coupling component proximal portion 630P supports a distal end of a conductive coil of insulated conductor 212, and a second surface 630P-2 of the other coupling component proximal portion 630P supports an outer insulation tube 211 that surrounds the conductive coil of insulated conductor 212.

Figure 7A:
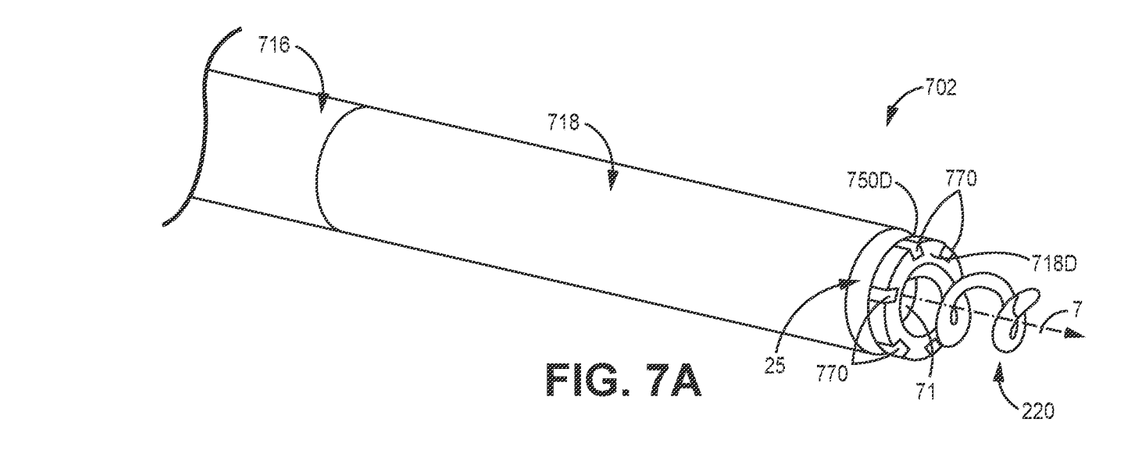
FIG. 7A is a perspective view of an electrode assembly that includes distal and proximal electrodes, according to some additional embodiments.
Figures 7B, 7C:
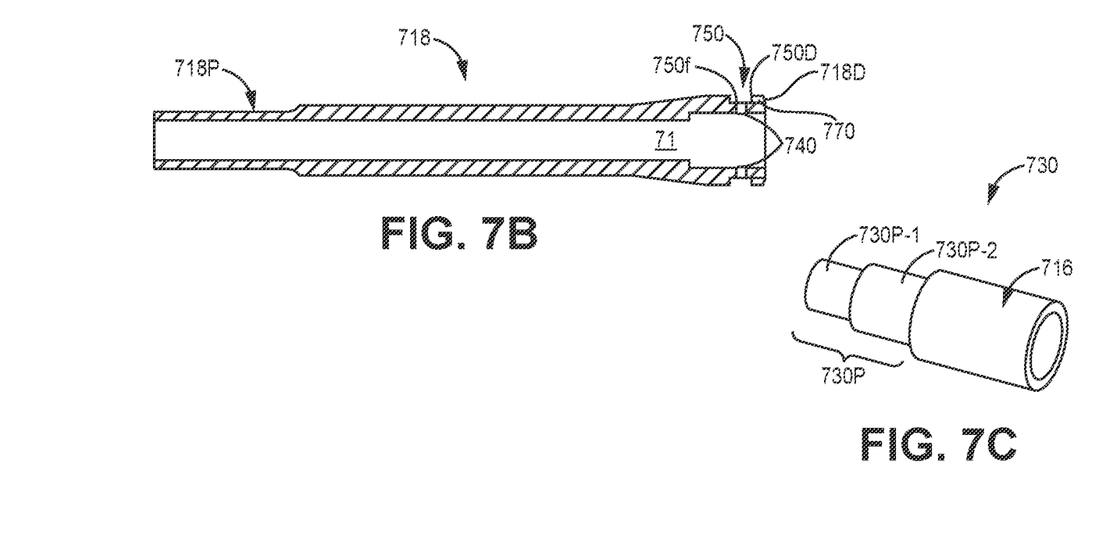
FIG. 7B is a longitudinal cross-section view of a sleeve of the FIG. 7A electrode assembly, according to some embodiments.
FIG. 7C is a perspective view of the proximal electrode of the FIG. 7A assembly, according to some embodiments.

FIG. 7A is a perspective view of an electrode assembly 702 that includes distal electrode 220 and proximal electrode 716, which is suitable for the delivery of pacing therapy, according to some additional embodiments. It should be noted that electrode assembly 702 may be incorporated by lead 200, in lieu of assembly 202, in a similar manner to that described above in conjunction with FIG. 2C. FIG. 7A illustrates a sleeve 718 of assembly 702, which defines a longitudinal axis 7 of assembly 702, and which includes a distal terminal end 718D, from which distal electrode 220 extends, for example, having the aforementioned proximal end 220P thereof mounted within an elongate bore 71 of sleeve 718 where the aforementioned conductive coupling component 222 is secured thereto as shown in FIG. 2C. FIG. 7A further illustrates electrode assembly 702 including the above-described steroid eluting component 25 that, similar to assembly 202, is seated in, and secured to, an external groove 750 of sleeve 718, which can be seen in the longitudinal cross-section view of sleeve 718 shown in FIG. 7B. With reference to FIGS. 7A-B, sleeve 718 further includes a plurality of channels 770 extending from a distal edge 750D of groove 750 to sleeve distal terminal end 718D so that channels 770 provide fluid communication between steroid eluting component 25 and an area distal to sleeve distal terminal end 718D, which surrounds distal electrode 220. FIG. 7B further illustrates sleeve 718 including one or more additional channels 740 that extend through a floor 750*f* of groove 750. Steroid eluting component 25 may be seated in, and secured to, groove 750 according to any of the methods described above for assemblies 202, 2021, and exemplary dimensions for groove 750 and channels 770, 740 may be the same as those recited above for sleeve 218. Although FIGS. 7A-B show channels 770 being formed in an outer surface of sleeve 718, according to alternate embodiments of sleeve 718, channels 770 may be formed along an inner surface thereof like channels 470 of sleeve 418 (FIG. 4). Furthermore, according to some embodiments, floors of some or all of channels 770 may be angled as shown for channel floor 270*f* of sleeve 218 in FIG. 3C. With further reference to FIGS. 7A-B, proximal electrode 716 of electrode assembly 702 may be in the form of a ring, being secured to a proximal end 718P of sleeve 718 by being mounted around an outer surface thereof. FIG. 7B shows the outer surface of sleeve proximal end 718P being recessed so that an outer surface of mounted proximal electrode 716 may be flush with an adjacent outer surface of sleeve 718, according to some embodiments. FIG. 7C is a perspective view of a component 730, which includes proximal electrode 716, according to some embodiments, and which may be constructed in a similar fashion to the above-described coupling component 630 that is employed in assembly 202 (FIGS. 2C and 6B). FIG. 7C illustrates component 730 including a distal portion that forms proximal electrode 716 and a stepped proximal portion 730P, wherein a first surface 730P-1 of component proximal portion 730P supports a distal end of a conductive coil of an elongate insulated conductor (e.g. insulated conductor 212 of FIG. 2C), and a second surface 730P-2 of component proximal portion 730P supports an outer insulation tube that surrounds the conductive coil of the insulated conductor (e.g., tube 211 of FIG. 2C).

In the foregoing detailed description, the invention has been described with reference to specific embodiments. However, it may be appreciated that various modifications and changes can be made without departing from the scope of the invention as set forth in the appended claims.

The invention claimed is:

1. An electrode assembly for an implantable medical device, the assembly comprising:
a sleeve defining a longitudinal axis of the assembly, the sleeve comprising a distal terminal end, an elongate bore extending along the axis proximally from a distal opening thereof at the distal terminal end, an external groove extending around the bore, and a plurality of channels, each channel of the plurality extending from the groove to the distal terminal end;
a distal electrode secured to the sleeve and extending distally from the distal terminal end of the sleeve;
a steroid eluting component seated within the external groove of the sleeve and being secured thereto; and
wherein, the plurality of channels of the sleeve provide fluid communication between the steroid eluting component and an area distal to the distal terminal end of the sleeve; and
wherein floors of some or all of the plurality of sleeve channels angle toward the longitudinal axis of the assembly, being closer to the axis at the distal terminal end of the sleeve.

2. The assembly of claim 1, wherein some or all of the plurality of sleeve channels extend from a distal edge of the sleeve groove.

3. The assembly of claim 1, wherein at least one channel of the plurality of sleeve channels extends through a floor of the sleeve groove.

4. The assembly of claim 1, wherein a portion of the steroid eluting component extends within at least one of the plurality of sleeve channels.

5. The assembly of claim 1, wherein some or all of the plurality of sleeve channels are formed in an outer surface of the sleeve.

6. The assembly of claim 1, wherein some or all of the plurality of sleeve channels are formed in an inner surface of the sleeve, the inner surface defining the sleeve bore.

7. The assembly of claim 1, wherein the sleeve is wholly formed from an insulative material.

8. The assembly of claim 7, further comprising a proximal electrode secured to a proximal end of the sleeve.

9. The assembly of claim 8, wherein the proximal electrode comprises a ring mounted around an outer surface of the sleeve.

10. The assembly of claim 8, further comprising a coupling component mounted within the sleeve bore, in proximity to the proximal end of the sleeve, the coupling component securing the proximal electrode to the sleeve.

11. An electrode assembly for an implantable medical device, the assembly comprising:
a sleeve defining a longitudinal axis of the assembly, the sleeve comprising a distal terminal end, an elongate bore extending along the axis proximally from a distal opening thereof at the distal terminal end, an external groove extending around the bore, and a plurality of channels, each channel of the plurality extending from the groove to the distal terminal end;
a distal electrode secured to the sleeve and extending distally from the distal terminal end of the sleeve;
a steroid eluting component seated within the external groove of the sleeve and being secured thereto; and
wherein, the plurality of channels of the sleeve provide fluid communication between the steroid eluting component and an area distal to the distal terminal end of the sleeve; and
wherein some or all of the plurality of sleeve channels are uniformly spaced apart from one another around the sleeve bore, the uniform spacing being about 60 degrees.

12. An electrode assembly for an implantable medical device, the assembly comprising:
a sleeve defining a longitudinal axis of the assembly, the sleeve comprising a distal terminal end, an elongate bore extending along the axis proximally from a distal opening thereof at the distal terminal end, an external groove extending around the bore, and a plurality of channels, each channel of the plurality extending from the groove to the distal terminal end;

a distal electrode secured to the sleeve and extending distally from the distal terminal end of the sleeve;

a steroid eluting component seated within the external groove of the sleeve and being secured thereto; and wherein, the plurality of channels of the sleeve provide fluid communication between the steroid eluting component and an area distal to the distal terminal end of the sleeve; and further comprising a conductive coupling component mounted within the sleeve bore and being secured to a proximal portion of the distal electrode that extends within the bore of the sleeve, and wherein the coupling component engages with an inner surface of the sleeve to prevent rotation of the distal electrode relative to the sleeve, the inner surface defining the sleeve bore.

13. An electrode assembly for an implantable medical device, the assembly comprising:

a sleeve defining a longitudinal axis of the assembly, the sleeve comprising a distal terminal end, an elongate bore extending along the axis proximally from a distal opening thereof at the distal terminal end, an external groove extending around the bore, and a plurality of channels, each channel of the plurality extending from the groove to the distal terminal end;

a distal electrode secured to the sleeve and extending distally from the distal terminal end of the sleeve;

a steroid eluting component seated within the external groove of the sleeve and being secured thereto;

wherein the plurality of channels of the sleeve provide fluid communication between the steroid eluting component and an area distal to the distal terminal end of the sleeve;

wherein the sleeve is wholly formed from an insulative material;

further comprising a proximal electrode secured to a proximal end of the sleeve;

wherein the proximal electrode comprises a ring mounted around an outer surface of the sleeve;

further comprising a coupling component mounted within the sleeve bore, in proximity to the proximal end of the sleeve, the coupling component securing the proximal electrode to the sleeve; and wherein:

the coupling component comprises a proximal portion and a distal portion, the distal portion of the coupling component being mounted within the sleeve bore, and the proximal portion of the coupling component extending proximally from the proximal end of the sleeve; and the proximal electrode comprises an elongate coil having a distal end coupled to the proximal portion of the coupling component.

14. An implantable medical electrical device comprising a connector, an elongate insulated conductor, and an electrode assembly, the connector including an electrical contact configured for connection to a pulse generator, the electrode assembly comprising a distal electrode coupled to the connector contact by the elongate insulated conductor, and the electrode assembly further comprising:

a sleeve defining a longitudinal axis of the assembly, the sleeve comprising a distal terminal end, an elongate bore extending along the axis proximally from a distal opening thereof at the distal terminal end, an external groove extending around the bore, and a plurality of channels, each channel of the plurality extending from the groove to the distal terminal end, and the distal electrode extending distally from the distal terminal end of the sleeve; and a steroid eluting component seated within the external groove of the sleeve and being secured thereto; and wherein the plurality of channels provide fluid communication between the steroid eluting component and an area distal to the distal terminal end of the sleeve; and wherein floors of some or all of the plurality of sleeve channels of the electrode assembly angle toward the longitudinal axis of the assembly, being closer to the axis at the distal terminal end of the sleeve.

15. The device of claim 14, wherein some or all of the plurality of sleeve channels of the electrode assembly extend from a distal edge of the sleeve groove.

16. The device of claim 14, wherein at least one channel of the plurality of sleeve channels of the electrode assembly extends through a floor of the sleeve groove.

17. The device of claim 14, wherein a portion of the steroid eluting component of the electrode assembly extends within at least one of the plurality of sleeve channels of the electrode assembly.

18. The device of claim 14, wherein some or all of the plurality of sleeve channels of the electrode assembly are formed in an outer surface of the sleeve.

19. The device of claim 14, wherein some or all the plurality of sleeve channels of the electrode assembly are formed in an inner surface of the sleeve, the inner surface defining the sleeve bore.

20. The device of claim 14, wherein the electrode assembly sleeve is wholly formed from an insulative material.

21. The device of claim 20, wherein the electrode assembly further comprises a proximal electrode secured to a proximal end of the assembly sleeve.

22. The device of claim 21, wherein the proximal electrode of the electrode assembly comprises a ring mounted around an outer surface of the assembly sleeve.

23. The device of claim 21, wherein the electrode assembly further comprises a coupling component mounted within the bore of the assembly sleeve, in proximity to the proximal end of the sleeve, the coupling component securing the proximal electrode of the assembly to the sleeve.

24. An implantable medical electrical device comprising a connector, an elongate insulated conductor, and an electrode assembly, the connector including an electrical contact configured for connection to a pulse generator, the electrode assembly comprising a distal electrode coupled to the connector contact by the elongate insulated conductor, and the electrode assembly further comprising:

a sleeve defining a longitudinal axis of the assembly, the sleeve comprising a distal terminal end, an elongate bore extending along the axis proximally from a distal opening thereof at the distal terminal end, an external groove extending around the bore, and a plurality of channels, each channel of the plurality extending from the groove to the distal terminal end, and the distal electrode extending distally from the distal terminal end of the sleeve; and a steroid eluting component seated within the external groove of the sleeve and being secured thereto; and wherein the plurality of channels provide fluid communication between the steroid eluting component and an area distal to the distal terminal end of the sleeve; and wherein some or all of the plurality of sleeve channels of the electrode assembly are uniformly spaced apart from one another around the sleeve bore, the uniform spacing being about 60 degrees.

25. An implantable medical electrical device comprising a connector, an elongate insulated conductor, and an electrode assembly, the connector including an electrical contact configured for connection to a pulse generator, the electrode assembly comprising a distal electrode coupled to the connector contact by the elongate insulated conductor, and the electrode assembly further comprising:
  a sleeve defining a longitudinal axis of the assembly, the sleeve comprising a distal terminal end, an elongate bore extending along the axis proximally from a distal opening thereof at the distal terminal end, an external groove extending around the bore, and a plurality of channels, each channel of the plurality extending from the groove to the distal terminal end, and the distal electrode extending distally from the distal terminal end of the sleeve; and
  a steroid eluting component seated within the external groove of the sleeve and being secured thereto; and
  wherein the plurality of channels provide fluid communication between the steroid eluting component and an area distal to the distal terminal end of the sleeve; and wherein:
  the electrode assembly further comprises a conductive coupling component mounted within the bore of the assembly sleeve and being secured to a proximal portion of the assembly distal electrode that extends within the bore of the sleeve; and
  the coupling component engages with an inner surface of the sleeve to prevent rotation of the distal electrode relative to the sleeve, the inner surface defining the sleeve bore.

26. An implantable medical electrical device comprising a connector, an elongate insulated conductor, and an electrode assembly, the connector including an electrical contact configured for connection to a pulse generator, the electrode assembly comprising a distal electrode coupled to the connector contact by the elongate insulated conductor, and the electrode assembly further comprising:
  a sleeve defining a longitudinal axis of the assembly, the sleeve comprising a distal terminal end, an elongate bore extending along the axis proximally from a distal opening thereof at the distal terminal end, an external groove extending around the bore, and a plurality of channels, each channel of the plurality extending from the groove to the distal terminal end, and the distal electrode extending distally from the distal terminal end of the sleeve; and
  a steroid eluting component seated within the external groove of the sleeve and being secured thereto;
  wherein the plurality of channels provide fluid communication between the steroid eluting component and an area distal to the distal terminal end of the sleeve;
  wherein the electrode assembly sleeve is wholly formed from an insulative material;
  wherein the electrode assembly further comprises a proximal electrode secured to a proximal end of the assembly sleeve;
  wherein the proximal electrode of the electrode assembly comprises a ring mounted around an outer surface of the assembly sleeve;
  wherein the electrode assembly further comprises a coupling component mounted within the bore of the assembly sleeve, in proximity to the proximal end of the sleeve, the coupling component securing the proximal electrode of the assembly to the sleeve; and wherein:
  the coupling component of the electrode assembly comprises a proximal portion and a distal portion, the distal portion of the coupling component being mounted within the bore of the assembly sleeve, and the proximal portion of the coupling component extending proximally from the proximal end of the sleeve; and
  the proximal electrode of the electrode assembly comprises an elongate coil having a distal end coupled to the proximal portion of the coupling component of the assembly.

27. A method for manufacturing an electrode assembly for an implantable medical device, the method comprising:
  forming a sleeve with an external groove extending around a bore of the sleeve and with a plurality of channels extending from the groove to a distal terminal end of the sleeve;
  mounting a proximal portion of a distal electrode within the bore of the sleeve so that a distal portion of the distal electrode extends distally from the distal terminal end of the sleeve; and
  seating a steroid eluting component within the groove of the sleeve so that the component is in fluid communication with an area distal to the distal terminal end of the sleeve via the channels of the sleeve; and further comprising:
  securing a conductive coupling component to the proximal portion of the distal electrode; and
  engaging the coupling component with an inner surface of the sleeve, the inner surface defining the bore of the sleeve, and a resulting engagement between the coupling component and the inner surface prevents rotation of the electrode with respect to the sleeve.

28. The method of claim 27, wherein:
the steroid eluting component comprises silicone rubber;
the sleeve comprises polyurethane; and
further comprising plasma treating the groove of the sleeve prior to seating the component within the groove.

29. The method of claim 27, wherein seating the steroid eluting component comprises insert molding the component into the groove of the sleeve.

* * * * *